(12) United States Patent
Bruun

(10) Patent No.: US 11,406,630 B2
(45) Date of Patent: Aug. 9, 2022

(54) NICOTINE POUCH

(71) Applicant: Fertin Pharma A/S, Vejle (DK)

(72) Inventor: Heidi Ziegler Bruun, Vejle Ost (DK)

(73) Assignee: NCP NextGen A/S, Vejle (DK)

( * ) Notice: Subject to any disclaimer, the term of this patent is extended or adjusted under 35 U.S.C. 154(b) by 0 days.

(21) Appl. No.: 16/065,986

(22) Filed: Jun. 25, 2018

(65) Prior Publication Data

US 2019/0255035 A1 Aug. 22, 2019

(30) Foreign Application Priority Data

Jun. 23, 2017 (WO) ................ PCT/DK2017/050211

(51) Int. Cl.
| | | |
|---|---|---|
| *A61K 31/465* | (2006.01) | |
| *A61K 47/22* | (2006.01) | |
| *A61K 47/38* | (2006.01) | |
| *A61K 9/00* | (2006.01) | |
| *A47L 9/28* | (2006.01) | |
| *A24B 15/16* | (2020.01) | |
| *A61K 47/12* | (2006.01) | |
| *A61K 47/32* | (2006.01) | |

(52) U.S. Cl.
CPC .......... *A61K 31/465* (2013.01); *A47L 9/2805* (2013.01); *A47L 9/2826* (2013.01); *A47L 9/2852* (2013.01); *A61K 9/006* (2013.01); *A61K 9/009* (2013.01); *A61K 9/0056* (2013.01); *A61K 47/22* (2013.01); *A61K 47/38* (2013.01); *A24B 15/16* (2013.01); *A47L 2201/02* (2013.01); *A47L 2201/04* (2013.01); *A61K 47/12* (2013.01); *A61K 47/32* (2013.01)

(58) Field of Classification Search
CPC .... A61K 31/465; A61K 9/0056; A61K 9/009; A61K 47/22; A61K 47/38; A61K 47/12; A61K 47/32; A24B 15/16
See application file for complete search history.

(56) References Cited

U.S. PATENT DOCUMENTS

| | | | | |
|---|---|---|---|---|
| 5,132,114 | A | * 7/1992 | Stanley | .................. A23G 3/368 |
| | | | | 424/435 |
| 5,783,207 | A | * 7/1998 | Stanley | .................. A23G 3/563 |
| | | | | 424/439 |
| 2012/0039981 | A1 | 2/2012 | Pedersen et al. | |
| 2013/0098377 | A1* | 4/2013 | Borschke | ............. A61K 31/465 |
| | | | | 131/270 |
| 2013/0160782 | A1* | 6/2013 | Axelsson | ............... A24B 15/14 |
| | | | | 131/352 |
| 2013/0251779 | A1* | 9/2013 | Svandal | ............... A61K 31/465 |
| | | | | 424/440 |
| 2014/0255452 | A1* | 9/2014 | Reddick | .................... B65B 1/04 |
| | | | | 424/400 |
| 2015/0272878 | A1* | 10/2015 | Nilsson | ................ A61K 31/465 |
| | | | | 424/400 |

FOREIGN PATENT DOCUMENTS

| | | |
|---|---|---|
| EP | 2177213 A1 | 4/2010 |
| WO | 2007104573 A2 | 2/2007 |
| WO | 2010031552 A1 | 3/2010 |
| WO | 2012134380 A1 | 10/2012 |

* cited by examiner

*Primary Examiner* — Doan T Phan
(74) *Attorney, Agent, or Firm* — St. Onge Steward Johnston & Reens LLC

(57) ABSTRACT

A pouch designed for administration of an active ingredient in the oral cavity is disclosed, the pouch containing a matrix composition including a combination of nicotine and a water-soluble composition.

21 Claims, No Drawings

NICOTINE POUCH

FIELD OF INVENTION

The invention relates to pouches comprising nicotine.

BACKGROUND OF THE INVENTION

Delivery of nicotine by smoking has many well-known drawbacks, particular health related problem, such as inclusion of carcinogenic substances.

However, tobacco substitutes also suffer from disadvantages, such as inadequate relief of cravings for the recovering smoker.

It is an object of the present invention to provide a nicotine containing pouch, e.g. as a tobacco substitute, which may solve the above problems.

SUMMARY

The invention relates to a pouch designed for administration of an active ingredient in the oral cavity, the pouch containing a matrix composition comprising a combination of nicotine and a water-soluble composition.

According to the invention, the matrix composition in the pouch comprises the nicotine as the active ingredient. One advantage of the invention may be that a highly suitable way of providing nicotine to a user is obtained having an effective release of nicotine. Due to the combination of nicotine with the water-soluble composition a completely releasable matrix composition may be obtained leading to an emptying of the pouch after release. Thereby, the user can, in a simple and intuitive way observe when the release of nicotine is release and the pouch may be removed from the oral cavity.

A further advantage of the invention is that uptake of nicotine while circumvention of the digestive system may be obtained, especially by taking advantage of the local high concentration of nicotine, leading to nicotine passing over the mucous membrane and into the bloodstream.

According to an advantageous embodiment of the invention said nicotine is provided as a complex between nicotine and an ion exchange resin.

An advantage of the above embodiment may be that an effective delivery of nicotine may be provided while keeping the nicotine relatively stable. Especially, in embodiments where said complex between the nicotine and the ion exchange resin is combined with using the water-soluble composition as a water-soluble carrier for said complex, particularly in the form of sugar and/or sugar alcohols, an effective and advantageous nicotine delivery may be obtained.

Thus, according to the above embodiment, the ion exchange resin is a carrier for the nicotine. One advantage of this embodiment may be that nicotine is provided in a relatively stable form.

According to an advantageous embodiment of the invention, said complex between nicotine and the ion exchange resin is nicotine polacrilex resin (NPR).

An advantage of the above embodiment may be that an effective delivery of nicotine may be provided while keeping the nicotine relatively stable. Especially, in embodiments where said NPR is combined with using the water-soluble composition as a water-soluble carrier for said NPR, particularly in the form of sugar and/or sugar alcohols, an effective and advantageous nicotine delivery may be obtained.

According to an advantageous embodiment of the invention the nicotine is provided as a salt.

According to an advantageous embodiment of the invention the nicotine is provided as its base form.

According to an advantageous embodiment of the invention said nicotine is extracted from tobacco.

According to an advantageous embodiment of the invention the water-soluble composition is a powder composition.

For example, when the water-soluble composition is a water-soluble carrier, it may be provided as a powder composition.

According to an advantageous embodiment of the invention the matrix composition is a powdered matrix composition.

According to an advantageous embodiment of the invention powdered matrix composition has an average particle size of below 1200 micrometer.

According to an advantageous embodiment of the invention powdered matrix composition has an average particle size above 1 micrometer.

According to an embodiment of the invention, the powdered matrix composition as an average particle size is between 1 and 1200 micrometer.

In an embodiment of the invention the powdered matrix composition has an average particle size of said powdered composition is between 1 and 400 micrometers.

According to an embodiment of the invention, the average powder diameter is larger than the average opening dimension of the pouch.

According to an embodiment of the invention, the matrix composition is in form of a powder comprising nicotine.

According to an embodiment of the invention, the matrix composition comprises nicotine polacrilex resin.

According to an advantageous embodiment of the invention the matrix composition comprises said water-soluble composition in an amount of 1.0-99.9 percent by weight.

According to an embodiment of the invention, the matrix composition comprises said water-soluble composition in an amount of between 2 and 70 percent weight of said matrix composition.

According to an embodiment of the invention, the matrix composition comprises said water-soluble composition in an amount of between 3 and 60 percent weight of said matrix composition.

According to an embodiment of the invention, the matrix composition comprises said water-soluble composition in an amount of between 5 and 50 percent weight of said matrix composition.

According to an embodiment of the invention, the matrix composition consists of said matrix composition and a sealed barrier enclosing said matrix composition.

According to an advantageous embodiment of the invention the water-soluble composition comprises a water-soluble carrier.

I.e. the carrier acts as a carrier for the nicotine. Thus, when for example the nicotine is provided as a complex between nicotine and an ion exchange resin, the water-soluble composition, according to the above embodiment, is a carrier for the nicotine-ion exchange resin complex.

According to an embodiment of the invention, the water-soluble composition is a water-soluble carrier.

One way of utilizing the water-soluble composition as a carrier may be by granulating said nicotine with said water soluble composition thereby obtaining granules comprising a combination of said nicotine and said water-soluble composition.

According to an advantageous embodiment of the invention the water-soluble composition comprises sugar alcohol.

In embodiments, where the water-soluble composition comprises or is a water-soluble carrier, the sugar alcohol may be the water-soluble carrier for the nicotine, or a part of such carrier for the nicotine, e.g. for nicotine provided as a complex with an ion exchange resin.

Alternatively, when the sugar alcohol is not a carrier for the nicotine, it may still be included as a sweetener.

According to an embodiment of the invention, said sugar alcohol may be a single type of sugar alcohol, or a mixture of two or more sugar alcohols.

According to an advantageous embodiment of the invention said sugar alcohol is selected from the group consisting of sorbitol, erythritol, xylitol, lactitol, maltitol, mannitol, hydrogenated starch hydrolyzates, isomalt, or any combination thereof.

According to an advantageous embodiment of the invention the matrix composition comprises sugar alcohol in an amount of 1.0-99.9 percent by weight of said matrix composition.

According to an embodiment of the invention the matrix composition comprises sugar alcohol in an amount of 20-99 percent by weight of said matrix composition, or in an amount of 60-95 percent by weight of said matrix composition.

According to an advantageous embodiment of the invention the water-soluble composition is sugar alcohol.

According to an embodiment of the invention the sugar alcohol forms a carrier.

According to an advantageous embodiment of the invention the water-soluble composition comprises sugar.

According to an advantageous embodiment of the invention said matrix composition comprises said sugar in an amount of 1.0 to 99.9 percent by weight of said matrix composition.

According to an embodiment of the invention the matrix composition comprises sugar in an amount of 20-99 percent by weight of said matrix composition, or in an amount of 60-95 percent by weight of said matrix composition.

According to an embodiment of the invention, the water-soluble composition comprises a combination of sugar and sugar alcohol.

According to an embodiment of the invention the matrix composition comprises sugar alcohol and sugar in a total amount of 20-99 percent by weight of said matrix composition, or in an amount of 60-95 percent by weight of said matrix composition.

Thus, according to an embodiment of the invention, the sugar as the water-soluble composition or part thereof may be a carrier for the nicotine, e.g. nicotine provided as a complex with an ion exchange resin. Alternatively, when the sugar is not a carrier for the nicotine, it may still be included as a sweetener.

According to an advantageous embodiment of the invention the matrix composition comprises a pH controlling agent.

An advantage of the above embodiment may be that the update of the nicotine may be increased by including a pH controlling agent, such as e.g. a buffering agent.

For example, the pH controlling agent may comprise or be a buffering agent, which may be adapted to ensure a relatively low pH value in the oral cavity above 7.

According to an advantageous embodiment of the invention the pH controlling agent is a buffering agent.

According to an advantageous embodiment of the invention the pH controlling agent is selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

According to an advantageous embodiment of the invention the pH controlling agent is a basic pH controlling agent, such as a basic buffering agent and/or such as Sodium carbonate, Sodium bicarbonate, Potassium carbonate or any combination thereof.

Various possible basic pH controlling agents and basic buffering agents are known and usable in the context of the above embodiment, whereby an increased pH value in the oral cavity may be obtained for facilitating uptake of nicotine across the mucous membrane.

According to an advantageous embodiment of the invention the matrix composition further comprises a release controlling composition.

One advantage of the above embodiment may be that by controlling the release of the nicotine, e.g. by means of controlling the supply of water in the form of saliva to the matrix composition, a modified release may be obtained, e.g. a delayed release.

According to an advantageous embodiment of the invention said release controlling composition is selected from the list consisting of metallic stearates, modified calcium carbonate, hydrogenated vegetable oils, partially hydrogenated vegetable oils, polyethylene glycols, polyoxyethylene monostearates, animal fats, silicates, silicates dioxide, talc, magnesium stearates, calcium stearates, fumed silica, powdered hydrogenated cottonseed oils, hydrogenated vegetable oils, hydrogenated soya oil and mixtures thereof.

According to an embodiment of the invention said modified calcium carbonate is made according to US patent application US 2012/0039981 A1, hereby incorporated by reference, particularly as in the examples therein.

According to an advantageous embodiment of the invention the release controlling composition is hydrophobic.

One advantage of the above embodiment may be that by controlling the release of the nicotine, e.g. by means of controlling the supply of water in the form of saliva to the matrix composition, a modified release may be obtained, e.g. a delayed release.

According to an advantageous embodiment of the invention said release controlling composition comprises one or more metallic stearates.

One advantage of the above embodiment may be that by controlling the release of the nicotine, e.g. by means of controlling the supply of water in the form of saliva to the matrix composition, a modified release may be obtained, e.g. a delayed release.

According to an advantageous embodiment of the invention said release controlling composition comprises magnesium stearate.

One advantage of the above embodiment may be that by controlling the release of the nicotine, e.g. by means of controlling the supply of water in the form of saliva to the matrix composition, a modified release may be obtained, e.g. a delayed release.

According to an advantageous embodiment of the invention said release controlling composition comprises calcium stearate.

One advantage of the above embodiment may be that by controlling the release of the nicotine, e.g. by means of controlling the supply of water in the form of saliva to the matrix composition, a modified release may be obtained, e.g. a delayed release.

According to an advantageous embodiment of the invention the matrix composition comprises said release controlling composition in an amount of between 1 and 20 percent by weight of said matrix composition.

According to an embodiment of the invention the matrix composition comprises said release controlling composition in an amount of between 3 and 15 percent by weight of said matrix composition.

According to an embodiment of the invention the matrix composition comprises magnesium stearate as said release controlling composition in an amount of between 3 and 15 percent by weight of said matrix composition.

According to an advantageous embodiment of the invention said matrix composition comprises a first portion and a second portion, wherein said first and second portions have different contents of said release controlling composition.

For example, the first and second portions may be provided as two separate powder fractions. The powder fractions may be premixed before being filled into the pouches allowing a relatively even distribution of powdered particles in from the two fractions in the pouch. Nevertheless, an advantage of the above embodiment may be that two different release profiles, one for each portion, may be combined to obtain a more complex total release profile not necessarily obtainable by a single uniform portion.

According to an advantageous embodiment of the invention said first portion release controlling composition and said second portion is free of release controlling composition.

According to an advantageous embodiment of the invention both of said first and second portions comprises nicotine.

According to an advantageous embodiment of the invention said first and second portions have different release profiles of nicotine.

According to an embodiment of the invention the characteristic opening dimension is adapted to the characteristic dimension of the matrix composition so as to retain the matrix composition inside the pouch before use.

According to an advantageous embodiment of the invention the pouch comprises a water-permeable membrane, comprising e.g. wowen or non-wowen fabric.

According to an advantageous embodiment of the invention the nicotine is physically or chemically bound to at least part of the matrix composition acting as a carrier.

According to an advantageous embodiment of the invention the nicotine have been granulated with the carrier.

According to an advantageous embodiment of the invention said matrix composition comprises nicotine in an amount of 0.1 to 30 percent by weight of said matrix composition.

According to an advantageous embodiment of the invention said matrix composition comprises nicotine in an amount of 0.5 mg to 10 mg.

According to an advantageous embodiment of the invention said nicotine is derived from tobacco.

According to an advantageous embodiment of the invention the pouch comprises a humectant.

In one embodiment, the humectant may be the water-soluble composition or be part of the water-soluble composition, whereas in other embodiments it may be provided as a separate composition in the pouch. When the water-soluble composition comprises a carrier or is part of a carrier, the humectant may be provided as the water-soluble carrier or as a separate composition in the pouch.

Suitable humectants may include one or more hygroscopic materials, such as cellulose, sugar alcohols, and other hygroscopic materials.

According to an advantageous embodiment of the invention the humectant comprises one or more from the list consisting of sugar alcohols, alginate, cellulose, such as microcrystalline cellulose, pectin, xanthan gum.

The humectant may in one embodiment be provided separately from the water-soluble composition.

The humectant may in one embodiment be provided by the water-soluble composition, i.e. the water-soluble composition is a humectant or comprises a humectant. When the water-soluble composition comprises a carrier, or is part of a carrier, the carrier may be a humectant.

According to an advantageous embodiment of the invention the pouch is free of tobacco.

DETAILED DESCRIPTION

Definitions

As used herein the term "pouch" is intended to mean a container typically formed by a web of a fibrous material enclosing a cavity. The pouch is pouch designed for administration of an active ingredient in the oral cavity, and thus it is adapted for oral use, it is non-toxic and not water-soluble. The fibrous material may e.g. form a woven or non-woven web or fabric. The pouch may for example be sealed by bonding two corresponding pieces of web or fabric to each other along their edges to form a cavity for the nicotine and the non-water-soluble composition. In order to release the nicotine, the pouch is made water-permeable so as to allow saliva from the oral cavity to penetrate the pouch and enter the cavity, where the saliva can come into contact with the nicotine, whereby the nicotine are released from the oral pouch.

As used herein the term "carrier" is intended to mean a substance that binds, physically or chemically an active ingredient. Unless otherwise stated, the term "carrier" refers to a carrier for said nicotine, whatever form the nicotine is provided on. Thus, the nicotine may be provided as a salt, a free base, or as a complex with an ion exchange resin, e.g. as NPR. When, for example, the nicotine is provided as NPR, the carrier, e.g. the water-soluble composition, is a carrier for the NPR, in the sense that the carrier binds the carrier, physically or chemically. Examples of carriers include water-soluble compositions, such as e.g. sugar alcohols, and sugar. For example, the water-soluble compositions may be granulated with the nicotine.

As used herein the term "nicotine" is preferably meant as nicotine extracted from tobacco. While the nicotine may be provided in several different forms e.g. as a complex with an ion exchange resin, as a salt, or as a free base, the nicotine is not provided in the form of tobacco or powdered tobacco.

As used herein the term "powder composition" refers to composition in the form of powder, i.e. as a particulate material having a relatively small particle size, for example between 1 and 1200 micrometer. Particularly, by powder composition is not meant a powdered tobacco. For example, a powdered matrix composition, i.e. the matrix composition as a powder, include a water-soluble composition and nicotine.

As used herein the term "humectant" is understood as a moistening agent used to attract moisture or water in the form of saliva. Humectants may typically include suitably hygroscopic compositions. In some cases, humectants may also be described as moistening agents, due to their role in attraction of moisture. Examples of humectants include cellulose, such as microcrystalline cellulose and other cellulose types disclosed herein, sugar alcohols, such as those disclosed herein, alginate, cellulose, such as microcrystalline cellulose, pectin, xanthan gum, etc.

As used herein the term "water-soluble composition" refers to a composition having a relatively high water-solubility, for example consisting of water-soluble substances having a water-solubility of more than 5 gram of water-soluble composition per 100 mL of water measured at 25 degrees Celsius and pH of 7.0. When referring to an "soluble" composition or substance, water-soluble is meant, unless otherwise stated. Likewise, when referring to "insoluble", water-insoluble is meant unless otherwise stated. The water-soluble composition is part of the matrix composition. In some embodiments, the water-soluble composition is part of a carrier or forms such system. The water-soluble composition does not include nicotine.

As used herein the term "matrix composition" is used as reference to the total content of the pouch, i.e. the entire composition enclosed by the pouch. Typically, it therefore corresponds to the pouch excluding the outer membrane of the pouch.

Typically, the pouches comprise openings, where the characteristic opening dimension is adapted to a characteristic dimension of the matrix composition so as to retain the matrix composition inside the pouch before use and/or to retain a part of the matrix composition, such as an insoluble composition, inside the pouch during use.

In order to obtain a pouch having suitable opening dimensions in view of the matrix composition to be used, the material for the pouch may be selected accordingly, e.g. comprising e.g. wowen or non-wowen fabric.

In other words, according to the various embodiments, the pouch forms a membrane allowing passage of saliva and prevents or inhibits passage of said matrix composition. The membrane of the pouch may be of any suitable material e.g. wowen or non-wowen fabric (e.g. cotton, fleece etc.), heat sealable non-wowen cellulose or other polymeric materials such as a synthetic, semi-synthetic or natural polymeric material. An example of suitable pouch material is paper made of pulp and a small amount of wet strength agent. A material suitable for use must provide a semi-permeable membrane layer to prevent the powder or composition from leaving the bag or pouch during use. Suitable materials are also those that do not have a significant impact on the release of nicotine from the pouch.

The powder is filled into pouches and is maintained in the pouch by a sealing. An ideal pouch is chemically and physically stable, it is pharmaceutically acceptable, it is insoluble in water, it is easy to fill with powder and seal, and it provides a semi-permeable membrane layer which prevent the powder from leaving the bag, but permit saliva and therein dissolved or sufficiently small suspended components from the powder in the pouch, such as nicotine, to pass through said pouch.

The pouch may be placed in the oral cavity by the user. Saliva then enters into the pouch, and the nicotine and other components, which are soluble in saliva, start to dissolve and are transported with the saliva out of the pouch into the oral cavity, where the nicotine may be absorbed.

According to an embodiment of the invention, the matrix composition may further comprise one or more enhancers.

In an embodiment of the invention, said enhancers are selected from the group consisting of bile salts, cetomacrogols, chelating agents, citrates, cyclodextrins, detergents, enamine derivatives, fatty acids, labrasol, lecithins, phospholipids, syntetic and natural surfactants, nonionic surfactants, cell envelope disordering compounds, solvents, steroidal detergents, chelators, solubilization agents, charge modifying agents, pH control agents, degradative enzyme inhibitors, mucolytic or mucus clearing agents, membrane penetration-enhancing agents, modulatory agents of epithelial junction physiology, vasodilator agents, selective transport-enhancing agents, or any combination thereof pH control agents include buffers.

In an embodiment of the invention, said enhancers are selected from the group consisting of cetylpyridinium chloride (CPC), benzalkonium chloride, sodium lauryl sulfate, polysorbate 80, Polysorbate 20, cetyltrimethylammonium bromide, laureth 9, sodium salicylate, sodium EDTA, EDTA, aprotinin, sodium taurocholate, saponins, bile salt derivatives, fatty acids, sucrose esters, azone emulsion, dextran sulphate, linoleic acid, labrafil, transcutol, urea, azone, nonionic surfactants, sulfoxides, sauric acid/PG, POE 23 lauryl ether, methoxysalicylate, dextran sulfate, methanol, ethanol, sodium cholate, Sodium taurocholate, Lysophosphatidyl choline, Alkylglycosides, polysorbates, Sorbitan esters, Poloxamer block copolymers, PEG-35 castor oil, PEG-40 hydrogenated castor oil, Caprocaproyl macrogol-8 glycerides, PEG-8 caprylic/capric, glycerides, Dioctyl sulfosuccinate, Polyethylene lauryl ether, Ethoxydiglycol, Propylene glycol, mono-di-caprylate, Glycerol monocaprylate, Glyceryl fatty acids ($C_8$-$C_{18}$) ethoxylated Oleic acid, Linoleic acid, Glyceryl caprylate/caprate, Glyceryl monooleate, Glyceryl monolaurate, Capryliccapric triglycerides, Ethoxylated nonylphenols, PEG-(8-50) stearates, Olive oil PEG-6, esters, Triolein PEG-6 esters, Lecithin, d-alpha tocopherol polyethylene glycol 1,000 succinate, Citric acid, Sodium citrate, BRIJ, Sodium laurate, 5-methoxysalicylic acid, Bile salts, Acetyl salicylate, ZOT, Docosahexaenoic acid, Alkylglycosides, Sodium glycocholate (GC-Na), Sodium taurocholate (TC-Na), EDTA, Choline salicylate, Sodium caprate (Cap-Na), N-lauryl-beta-D-maltopyranoside (LM), Diethyl maleate, Labrasol, Sodium salicylate, Mentol, Alkali metal alkyl sulphate, Sodium lauryl sulphate, Glycerin, Bile acid, Lecithin, phosphatidylcholine, phosphatidylserine, sphingomyelin, phophatidylethanolamine, cephalin, lysolecithin, Hyaluronic acid: alkalimetal salts, sodium, alkaline earth and aluminum, Octylphenoxypolyethoxyethanol, Glycolic acid, Lactic acid, Chamomile extract, Cucumber extract, Borage oil, Evening primrose oil, Polyglycerin, Lysine, Polylysine, Triolein, Monoolein, Monooleates, Monolaurates, Polydocanol alkyl ethers, Chenodeoxycholate, Deoxycholate, Glycocholic acid, Taurocholic acid, Glycodeoxycholic acid, Taurodeoxycholic acid, Sodium glycocholate, Phosphatidylcholine, Phosphatidylserine, Sphingomyelin, Phosphatidylethanolamine, Cephalin, Lysolecithin, Alkali metal hyaluronates, Chitosan, Poly-L-arginine, Alkyl glucoside, Saccharide alkyl ester, Fusidic acid derivatives, Sodium taurdihydrofusidate (STDHF), L-α-phosphatidylcholine Didecanoyl (DDPC), Nitroglycerine, nitropruside, N005 [3-(2-hydroxy-1-(methyl-ethyl)-2-nitrosohydrazino)-1-propanamine], NOC12 [iV-ethyl-2-(1-ethyl-hydroxy-2-nitrosohydrazino)-ethanamine, SNAP [S-nitroso-N-acetyl-DLpenicillamine, NORI, NOR4, deacylmethyl sulfoxide, atone, salicylamide, glyceryl-1,3-diacetoacetate, 1,2-isopropylideneglycerine-3-acetoacetate), Amino acids, Amino acid salts, monoaminocarboxlic acids, Glycine, alanine, phenylalanine, proline, hydroxyproline, hydroxyamino acids, serine, acidic amino acids, aspartic acid, Glutamic acid, Basic amino acids, Lysine, N-acetylamino acids, N-acetylalanine, N-acetylphenylalanine, TM-acetylserine, N-acetylglycine, N-acetyllysine, N-acetylglutamic acid, N-acetylproline, N-acetylhydroxyproline, lactic acid, malic acid and citric acid and alkali metal salts thereof, pyrrolidonecarboxylic acids, alkylpyrrolidonecarboxylic acid esters, N-alkylpyrrolidones, proline acyl esters, sodium lauryl phosphate, sodium lauryl sulphate, sodium oleyl phosphate, sodium myristyl sulphate, polyoxyethylene alkyl ethers, polyoxyethylene alkyl esters, and caproic acid, alkylsaccharide, fusidic acid, polyethylene glycol, cetyl alcohol, polyvinylpyrolidone, Polyvinyl alcohol, Lanolin alcohol, Sorbitan monooleate, Ethylene glycol tetraacetic acid, Bile acid conjugate with taurine, Cholanic acid and salts, Cyclodextran, Cyclodextrin, Cyclodextrin (beta), Hydroxypropyl-β-cyclodetran, Sulfobutylether-β-cyclodextran, Methyl-β-cyclodextrin, Chitosan glutamate, Chitosan acetate, Chitosan hydrochloride, Chitosan hydrolactate, 1-O-alkyl-2-hydroxy-sn-glycero-3-phosphocholine, 3-O-alkyl-2-acetoyl-sn-glycero-1-phosphocholine, 1-O-alkyl-2-O-acetyl-sn-glycero-3-phospho(N,N,N-trimethyl)hexanolamine, Propylene glycol, Tetradecylmaltoside (TDM), Sucrose dedecanoate.

According to an embodiment of the invention, the enhancer comprises one or more pH control agent, such as a buffering agent.

In an embodiment of the invention, said pH control agents are selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate. Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

According to various embodiments of the invention, one or more sugar alcohols may be included in the pouch as part of the matrix composition, e.g. as a carrier or part thereof, as a humectant, or as a sweetener. Suitable sugar alcohols include sugar alcohols selected from the group of sorbitol, erythritol, xylitol, lactitol, maltitol, mannitol, hydrogenated starch hydrolyzates, isomalt, or any combination thereof.

In an embodiment of the invention the pouch comprises high intensity sweetener.

Preferred high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

In an embodiment of the invention, the pouch comprises bulk sweeteners including sugar and/or sugarless components.

In an embodiment of the invention, the pouch comprises bulk sweetener in the amount of 1.0 to about 99.9% by weight of the pouch, more typically constitute 20 to about 98% by weight of the pouch, and more commonly, 30 to 95% by weight of the pouch. Bulk sweeteners may function both as a sweetener and also as a humectant.

The sweeteners may often support the flavor profile of the pouch.

Sugar sweeteners generally include, but are not limited to saccharide-containing components commonly known in the art of pouches, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

The sweetener can be used in combination with sugarless sweeteners. Generally, sugarless sweeteners include components with sweetening characteristics but which are devoid of the commonly known sugars and comprise, but are not limited to, sugar alcohols, such as sorbitol, mannitol, xylitol, hydrogenated starch hydrolyzates, maltitol, isomalt, erythritol, lactitol and the like, alone or in combination. These sugarless sweeteners may also be included as a humectant.

In an embodiment of the invention the pouch comprises flavor. Flavor may typically be present in amounts between 0.01 and 10% by weight of the total composition of the pouch, such as between 0.01 and 5% by weight of the total composition.

Non-exhaustive examples of flavors suitable in embodiments of the present invention are coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

In various embodiments of the invention, the matrix composition comprises a release controlling composition for controlling the release of the matrix composition and/or parts thereof, especially the nicotine.

The release controlling composition may, according to various embodiments, be selected group consisting of metallic stearates, modified calcium carbonate, hydrogenated vegetable oils, partially hydrogenated vegetable oils, polyethylene glycols, polyoxyethylene monostearates, animal fats, silicates, silicates dioxide, talc, magnesium stearates, calcium stearates, fumed silica, powdered hydrogenated cottonseed oils, hydrogenated vegetable oils, hydrogenated soya oil and mixtures thereof. Particularly, metallic stearates, such as magnesium stearate, may be advantageous.

The release controlling composition may be added to the matrix composition in various ways.

For example, the release controlling composition may be added by full powder mixture during the last few minutes of the final mixing.

Alternatively, the release controlling composition may be added after the granulation steps on a granulation premix.

Still further, the release controlling composition may be added only as a fraction of the matrix composition so two different release profiles of nicotine is achieved. Even further two or more fractions of the matrix composition may comprise different amounts of the release controlling composition, if any, thereby providing a more complex and tailored release profile of nicotine.

The release controlling composition, such as magnesium stearate, may have a sealing effect and can be used to control the release of the nicotine and the solubility of the pouch.

According to an embodiment of the invention, the pouch comprises polyvinylpyrrolidone (PVP).

One advantage of the above embodiment may be that a more uniform composition may be obtained.

EXAMPLES

The following examples are illustrative of the present invention and should not be considered as limiting the scope of the invention.

Examples 1-3 illustrate various raw materials and methods for preparing intermediate ingredients.

Examples 4-10 disclose a number of different pouches and their respective compositions.

Example 1

Preparation of Nicotine in a Powder Composition

The manufacture of a nicotine powder composition can be made in many different ways known to a person skilled in the art. Depending on the combinations the manufacturing steps will vary.

As illustrated in the following examples, nicotine can be added, sorbed, mixed or granulated on different carriers such as resin, modified calcium carbonate or sugar alcohols etc. Nicotine may be in form of a salt, such as nicotine bitartrate or nicotine polacrilex resin.

Example 2

Preparation of Pouches Designed for Administration of Nicotine

The material of the pouches is heat sealable non-wowen cellulose, such as long fiber paper. Pouches that are not in form of non-woven cellulose fabric may also be used according to the invention.

The powder is filled into pouches and is maintained in the pouch by a sealing.

Example 3

Preparation of Pouches with Nicotine—Sugar Alcohol Carrier

Nicotine used in example 3 is obtained in accordance with example 1. The pouches described in example 2 are used.

Herein, target fill weight 400 mg powder per pouch. Alternatively, target fill weights of e.g. 250 mg or 800 mg could be used.

Example 3.1

The nicotine and sugar alcohol are weighed. The nicotine is slowly added to the sugar alcohol (e.g. sorbitol, xylitol, maltitol, isomalt, mannitol, or mixtures thereof) powder under stirring (Kitchenaid mixer operated at about 30 RPM in about 30 minutes). The resulting granulate is sieved and placed on a tray. The resulting powder is dried at ambient temperature overnight and is thereafter sieved to obtain a premix.

The obtained premix is mixed with the remaining ingredient to obtain a final powder composition, which is manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. sugar alcohols, these further humectants are added in the same manner as magnesium stearate.

Example 3.2

The premix from example 3.1 is mixed with the remaining powder ingredient (sugar alcohol (e.g. sorbitol, xylitol, maltitol, isomalt, mannitol, or mixtures thereof), high intensive sweetener, and flavors) to obtain a homogenous powder composition.

Kollidon 25 (polyvinylpyrrolidone) is added together with the liquid flavor to form a homogeneous granulation solution.

The granulation solution is slowly added to the powder mixture under stirring (Kitchenaid mixer operated at about 30 RPM in about 30 minutes). The resulting granulate is sieved and placed on a tray. The resulting powder is dried at ambient temperature overnight and is thereafter sieved to obtain a final powder composition.

The obtained final powder composition is manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. sugar alcohols, these further humectants are added in the same manner as magnesium stearate.

Example 3.3

Any cationic ion exchange resin complex (preferable a non-ionic pharmaceutical grade resin) may in principle be used. The resin is capable of binding anionic molecules at the ion exchange sites.

The nicotine-resin complex used herein is made by mixing water, nicotine, resin (for example Amberlite®IRP64) and optionally glycerin. When a homogeneous solution is obtained and all nicotine has been bound by the ion exchange resin the pressure is reduced and the obtained mixture is concentrated in vacuum at elevated temperature affording the desired complex as a powder. The nicotine-resin complex is sieved.

The obtained nicotine-resin complex powder is mixed with the remaining ingredients to obtain a final powder composition.

The final powder composition is manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. sugar alcohols, these further humectants are added in the same manner as magnesium stearate.

Example 3.4

A powder composition obtained the same way as the final powder competition in example 3.3. Thereafter, polyvinylpyrrolidone (Kollidon 25) is added to form a granulation solution. The resulting granulate is sieved and placed on a tray. The resulting powder is dried at ambient temperature overnight and is thereafter sieved to obtain a final powder composition.

The final powder composition manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. MCC and/or sugar alcohols, these further humectants are added in the same manner as magnesium stearate.

Example 3.5

To obtain a premixture of nicotine and modified calcium carbonate, 1 part by weight of pure nicotine is mixed with 2 parts by weight of natural calcium carbonate modified to a surface area at approximately 40 $m^2/g$ to form a free-flowing material. A Kitchenaid mixer operated at about 30 RPM in about 30 minutes has been used for the mixing. The resulting granulate is sieved.

The obtained premixture of nicotine and modified calcium carbonate (made according to US patent application US 2012/0039981 A1) is mixed with the remaining ingredients to obtain a final powder composition.

The final powder composition is manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. sugar alcohols, these further humectants are added in the same manner as magnesium stearate.

Example 3.6

A powder composition obtained the same way as the final powder competition in example 3.5. Thereafter, polyvinylpyrrolidone (Kollidon 25) is added to form a granulation solution. The resulting granulate is sieved and placed on a tray. The resulting powder is dried at ambient temperature overnight and is thereafter sieved to obtain a final powder composition.

The final powder composition manually filled into pouches (target fill weight 400 mg powder per pouch). The pouch of example 2, made from long fiber paper, is used.

Magnesium stearate, if any, is added by full powder mixture during the last few minutes of the final mixing. When including smaller amounts of further humectants, apart from e.g. sugar alcohols, these further humectants are added in the same manner as magnesium stearate.

Example 3.7

The nicotine-resin complex used herein is made by mixing water, nicotine, resin (Amberlite®IRP64) and glycerin. When a homogeneous solution is obtained and all nicotine has been bound by the ion exchange resin the pressure is reduced and the obtained mixture is concentrated in vacuum at elevated temperature affording the desired complex as a powder. The nicotine-resin complex is sieved.

Any cationic ion exchange resin complex (preferable a non-ionic pharmaceutical grade resin) may in principle be used. The resin is capable of binding anionic molecules at the ion exchange sites.

The obtained nicotine-resin complex powder is mixed using a Turbula mixer for 6 minutes (speed 49 rpm) with the remaining ingredients to obtain a final powder composition.

The final powder composition is filled into pouches (target fill weight 400 mg powder per pouch). The pouch of example 2, made from long fiber paper, is used. The powder is filled into pouches and is maintained in the pouch by a sealing.

Magnesium stearate, if any, is added by full powder mixture during the last few minutes of the final mixing. When including smaller amounts of further humectants, apart from e.g. sugar alcohols, these further humectants are added in the same manner as magnesium stearate.

Example 3.8

Nicotine bitartrate xH2O is mixed using a Turbula mixer for 6 minutes (speed 49 rpm) with the remaining ingredients to obtain a final powder composition.

The final powder composition is filled into pouches (target fill weight 400 mg powder per pouch). The pouch material of example 2, made from long fiber paper, is used. The powder is filled into pouches and is maintained in the pouch by a sealing.

Magnesium stearate, if any, is added by full powder mixture during the last few minutes of the final mixing. When including smaller amounts of further humectants, apart from e.g. sugar alcohols, these further humectants are added in the same manner as magnesium stearate.

Example 4

Preparation of Pouches with Nicotine—Sugar Alcohol Carrier

TABLE 1

| | Pouch no. | | | | | |
|---|---|---|---|---|---|---|
| | 101 | 102 | 103 | 104 | 105 | 106 |
| Method example | 3.1 | 3.1 | 3.1 | 3.1 | 3.1 | 3.2 |
| Raw material | Content in weight percent | | | | | |
| Nicotine | 0.50* | 0.50* | 0.50* | 0.50* | 0.50* | 0.50* |
| Sorbitol | 98 | — | — | — | — | — |
| Xylitol | — | 98 | — | — | — | — |
| Maltitol | — | — | 98 | — | — | — |
| Isomalt | — | — | — | 98 | — | — |
| Mannitol | — | — | — | — | 98 | 90 |
| Flavor | 1.5 | 1.5 | 1.5 | 1.5 | 1.5 | 1.5 |
| HIS | 0.05 | 0.05 | 0.05 | 0.05 | 0.05 | 0.05 |
| PVP | — | — | — | — | — | 8 |
| Total | 100 | 100 | 100 | 100 | 100 | 100 |

Nicotine pouch;
Nicotine used 100% pure.
*0.5% Nicotine corresponds to 2 mg Nicotine/pouch.
Pouches contain 400 mg per piece.
HIS = High intense sweetener is sucralose.
Flavor is pepper mint flavor.
PVP = polyvinylpyrrolidone, Kollidon 25.

As shown in table 1, different sugar alcohols may be used, optionally in combination with PVP.

Example 5

Preparation of Pouches with Magnesium Stearate

TABLE 2

| | Pouch no. | | | |
|---|---|---|---|---|
| | 107 | 108 | 109 | 110 |
| Method example | 3.1 | 3.1 | 3.1 | 3.1 |
| Raw material | Content in weight percent | | | |
| Nicotine | 0.50* | 0.50* | 0.50* | 0.50* |
| Mannitol | 93 | 90 | 88 | 78 |
| Flavour | 1.5 | 1.5 | 1.5 | 1.5 |
| HIS | 0.05 | 0.05 | 0.05 | 0.05 |
| Sodiumhydrogen carbonate | — | 1.0 | — | — |
| Sodium carbonate | — | 2.0 | — | — |
| MgSt | 5 | 5 | 10 | 20 |
| Total | 100 | 100 | 100 | 100 |

Nicotine pouch; Nicotine used 100% pure.
*0.5% Nicotine corresponds to 2 mg Nicotine/pouch.
Pouches contain 400 mg per piece.
HIS = High intense sweetener may for example be sucralose.
Flavor may for example be pepper mint flavor.
MgSt is magnesium stearate and is added as a releasing controlling composition.

As shown in table 2, magnesium stearate may be included in different amounts. Also, buffer (here Sodium hydrogen carbonate and Sodium carbonate) may be added. Magnesium stearate has a sealing effect and can be used to control the release of Nicotine and the solubility of the pouch.

Example 6

Preparation of Pouches with Premix of Resin and Modified Calcium Carbonate

TABLE 3

| | Pouch no. | | | | |
|---|---|---|---|---|---|
| | 111 | 112 | 113 | 114 | 115 |
| Method cf. example | 3.3 | 3.3 | 3.3 | 3.4 | 3.4 |
| Raw material | Content in weight percent | | | | |
| Nicotine | 0.50* | 0.50* | 0.50* | 0.50* | 0.50* |
| Mannitol | 96.0 | 95.0 | 92.0 | 84.0 | 79.0 |
| Ion exchange resin | 2.0 | 2.0 | 2.0 | 2.0 | 2.0 |
| Glycerin | — | 0.8 | 0.8 | 0.8 | 0.8 |
| Flavor | 1.5 | 1.5 | 1.5 | 1.5 | 1.5 |
| HIS | 0.05 | 0.05 | 0.05 | 0.05 | 0.05 |
| Sodiumhydrogen carbonate | — | — | 1.0 | 1.0 | 1.0 |
| Sodium carbonate | — | — | 2.0 | 2.0 | 2.0 |
| PVP | — | — | — | 8.0 | 8.0 |
| MgSt | — | — | — | — | 5.0 |
| Total | 100 | 100 | 100 | 100 | 100 |

Nicotine pouch; Nicotine used 100% pure.
*0.5% Nicotine corresponds to 2 mg Nicotine/pouch.
Pouches contain 400 mg per piece.
Ion exchange resin is an Amberslite ™IRP64.
HIS = High intense sweetener may for example be sucralose.
Flavor may for example be pepper mint flavor.
PVP = polyvinylpyrrolidone, Kollidon 25.
MgSt is magnesium stearate and is added as a releasing controlling composition.

TABLE 4

| | Pouch no. | | | | |
|---|---|---|---|---|---|
| | 111 | 112 | 113 | 114 | 115 |
| Method cf. example | 3.3 | 3.3 | 3.3 | 3.4 | 3.4 |
| Raw material | Content in weight percent | | | | |
| Nicotine | 0.50* | 0.50* | 0.50* | 0.50* | 0.50* |
| Mannitol | 96.0 | 95.0 | 92.0 | 84.0 | 79.0 |
| Ion exchange resin | 2.0 | 2.0 | 2.0 | 2.0 | 2.0 |
| Glycerin | — | 0.8 | 0.8 | 0.8 | 0.8 |
| Flavor | 1.5 | 1.5 | 1.5 | 1.5 | 1.5 |
| HIS | 0.05 | 0.05 | 0.05 | 0.05 | 0.05 |
| Sodiumhydrogen carbonate | — | — | 1.0 | 1.0 | 1.0 |
| Sodium carbonate | — | — | 2.0 | 2.0 | 2.0 |
| PVP | — | — | — | 8.0 | 8.0 |
| MgSt | — | — | — | — | 5.0 |
| Total | 100 | 100 | 100 | 100 | 100 |

Nicotine pouch; Nicotine used 100% pure.
*0.5% Nicotine corresponds to 2 mg Nicotine/pouch.
Pouches contain 400 mg per piece.
Ion exchange resin is an Amberslite ™IRP64.
HIS = High intense sweetener may for example be sucralose.
Flavor may for example be pepper mint flavor.
PVP = polyvinylpyrrolidone, Kollidon 25.
MgSt is magnesium stearate and is added as a releasing controlling composition.

As shown in table 3 and 4, different pouches with and without PVP, MgSt, and buffer can be made, all with or without modified CaCO3.

Example 7

Preparation of Pouches with Different Concentrations of Nicotine

TABLE 5

| | Pouch no. | | | | | |
|---|---|---|---|---|---|---|
| | 120 | 121 | 122 | 123 | 124 | 125 |
| Method example | 3.2 | 3.2 | 3.2 | 3.2 | 3.2 | 3.2 |
| Amount of nicotine | 0.5 mg | 1 mg | 2 mg | 4 mg | 6 mg | 8 mg |
| Raw material | Content in weight percent | | | | | |
| Nicotine | 0.13 | 0.25 | 0.50 | 1.0 | 1.5 | 2.0 |
| Isomalt | 85.0 | 85.0 | 85.0 | 84.0 | 84.0 | 83.0 |
| Flavor | 1.5 | 1.5 | 1.5 | 1.5 | 1.5 | 1.5 |
| HIS | 0.05 | 0.05 | 0.05 | 0.05 | 0.05 | 0.05 |

TABLE 5-continued

| | Pouch no. | | | | | |
|---|---|---|---|---|---|---|
| | 120 | 121 | 122 | 123 | 124 | 125 |
| PVP | 8.0 | 8.0 | 8.0 | 8.0 | 8.0 | 8.0 |
| MgSt | 5.0 | 5.0 | 5.0 | 5.0 | 5.0 | 5.0 |
| Total | 100 | 100 | 100 | 100 | 100 | 100 |

Nicotine pouch;
Nicotine is used in different dosage from 0.5-8 mg nicotine/pouch-Nicotine pure 100% has been used.
Pouches contain 400 mg per piece.
HIS = High intense sweetener may for example be sucralose.
Flavor may for example be pepper mint flavor.
PVP = polyvinylpyrrolidone, Kollidon 25.
MgSt is magnesium stearate and is added as a releasing controlling composition.

As shown in table 5, pouches with different total amount of nicotine can be made.

In this example, pure nicotine was used. Alternatively, nicotine in other forms, such as NPR or nicotine premixed with modified calcium carbonate, may be used.

Example 8

Preparation of Pouches with Humectants

TABLE 6

| | Pouch no. | | | |
|---|---|---|---|---|
| | 126 | 127 | 128 | 129 |
| Method example | 3.1 | 3.1 | 3.1 | 3.1 |
| Raw material | Content in weight percent | | | |
| Nicotine | 0.50* | 0.50* | 0.50* | 0.50* |
| Isomalt | 93.0 | 91.0 | 91.0 | 91.0 |

TABLE 6-continued

| | Pouch no. | | | |
|---|---|---|---|---|
| | 126 | 127 | 128 | 129 |
| Flavor | 1.50 | 1.50 | 1.50 | 1.50 |
| HIS | 0.05 | 0.05 | 0.05 | 0.05 |
| Glycerol | — | 2.00 | — | — |
| Sodium alginate | — | — | 2.00 | — |
| Pectin | — | — | — | 2.00 |
| MgSt | 5.00 | 5.00 | 5.00 | 5.00 |
| Total | 100 | 100 | 100 | 100 |

Nicotine pouch; Nicotine used 100% pure.
*0.5% Nicotine corresponds to 2 mg Nicotine/pouch.
Pouches contain 400 mg per piece
HIS = High intense sweetener may for example be sucralose.
Flavor may for example be pepper mint flavor.
MgSt is magnesium stearate and is added as a releasing controlling composition.

As shown in table 6, various further humectants, other than sugar alcohols may also be included. Humectants attract the saliva from the mouth and make sure that water is available in the pouch. Increased water increase the release.

In this example, pure nicotine was used. Alternatively, nicotine in other forms, such as NPR or nicotine premixed with modified calcium carbonate, may be used.

Example 9

Preparation of Pouches with Nicotine Polacrilex Resin (NPR) or Nicotine Bitartrate (NBT)

TABLE 7

| | Pouch no. | | | | | |
|---|---|---|---|---|---|---|
| | 130 | 131 | 132 | 133 | 134 | 135 |
| Method Example | 3.7 | 3.8 | 3.8 | 3.8 | 3.7 | 3.7 |
| References | 9621-05-001 | 9621-05-002 | 9621-05-003 | 9621-05-004 | 9621-05-005 | 9621-05-006 |
| Amount of nicotine | 3 mg | 3 mg | 3 mg | 3 mg | 3 mg | 3 mg |
| Raw material | Content in weight percent | | | | | |
| NPR | 4.75 | — | — | — | 4.75 | 4.75 |
| NBT | — | 2.30 | 2.30 | 2.30 | — | — |
| Isomalt GalenIQ 720 | 30.06 | 31.29 | — | 41.41 | 40.19 | 21.28 |
| Zerose TM erythritol | — | — | 31.29 | — | — | 21.28 |
| Sodium carbonate and. | 2.50 | 2.50 | 2.50 | 2.50 | 2.50 | 2.50 |
| Sodium bicarbonate | 4.00 | 4.00 | 4.00 | 4.00 | 4.00 | 4.00 |
| Novamint Peppermint | 2.50 | 2.50 | 2.50 | 2.50 | 2.50 | — |
| Menthol | 1.00 | 1.00 | 1.00 | 1.00 | 1.00 | — |
| Eucalyptos | — | — | — | — | — | 3.50 |
| Acesulfame potassium | 0.13 | 0.13 | 0.13 | 0.13 | 0.13 | 0.13 |
| Avicel PH-102 | 25.00 | 25.00 | 25.00 | — | — | — |
| Aerosil 200 | — | — | — | 1.00 | 1.00 | — |
| Isomalt | 30.06 | 31.29 | — | 41.41 | 40.19 | 21.28 |
| Zerose TM erythritol | — | — | 31.29 | — | — | 21.28 |
| MgSt | — | — | — | 3.75 | 3.75 | — |
| Total | 100 | 100 | 100 | 100 | 100 | 100 |

Nicotine pouch;
NPR is nicotine polacrilex resin where the resin is Amberlite ™ IRP64.
NBT is nicotine bitartrate.
Pouches contain 400 mg per piece.
MgSt is magnesium stearate and is added as a releasing controlling composition.

Example 10

Combined Examples

The above examples may be combined so as to obtain different release profiles of nicotine in the same pouch. For example, pure nicotine bound to sugar alcohols may be combined with nicotine bound to ion exchange resin, such as NPR.

Also, the pouch may contain two powdered fractions of matrix composition, a first fraction without releasing controlling composition and a second fraction comprising releasing controlling composition, such as MgSt. This may also be combined with resin complex and/or nicotine pre-mixed with modified calcium carbonate.

Example 11

Evaluation

The pouches produced were evaluated and found highly suitable as delivery vehicles for nicotine.

Release Studies

Dissolution profiles of six pouches from Example 9 and two pouches of marketed product (Zyn™ Pouches 3 and 6 mg CoolMint) are presented in following table:

TABLE 8

Dissolution Profile [% release] of nicotine pouches - 3 mg in pH 7.4 Phosphate Buffer, Agitation: 100 rpm, Apparatus: USP Type I (Basket), Volume: 900 ml. Results for API (nicotine) as both NPR and NBT.

| Time | | Samples | | | | | |
|---|---|---|---|---|---|---|---|
| [min] | API | 0 | 8 | 16 | 30 | 60 | 120 |
| 130 | NPR | 0 | 59.9 | 85.1 | 97.5 | 101 | 102 |
| 131 | NBT | 0 | 80.1 | 89.1 | 94.4 | 95.9 | 96.6 |
| 132 | NBT | 0 | 72.0 | 89.4 | 97.1 | 100 | 99.8 |
| 133 | NBT | 0 | 34.7 | 45.4 | 56.9 | 72.9 | 88.4 |
| 134 | NPR | 0 | 14.2 | 25.8 | 41.4 | 61.7 | 80.6 |
| 135 | NPR | 0 | 65.6 | 83.0 | 90.6 | 94.4 | 95.2 |
| Zyn 3 mg | NBT | 0 | 85.3 | 92.9 | 96.3 | 97.1 | 97.5 |
| Zyn 6 mg | NBT | 0 | 88.0 | 96.2 | 97.3 | 98.5 | 98.5 |

Observations

Overall, the release profiles of pouches 130-135 differ compared to the release profile of the marketed product Zyn™. Pouches 130-132 show slightly slower release than the marketed product Zyn™ after 8 to 16 minutes. However, after about 30 minutes, pouches 130 and 132 have released more nicotine than the marketed product Zyn™ 3 mg.

The pouches with NPR show slower release compared to NBT (130 vs. 131), in particular after 8 minutes. However, after 30 minutes pouches with NPR (130) exhibit a release of nicotine that is greater than both the marketed products and pouches 131-135. This finding is surprising and was not expected.

Pouches 133 and 134, with a content of magnesium stearate and Aerosil 200, exhibit significantly slower release than the marketed product Zyn™. This is highly surprising, and it appears that magnesium stearate is suitable for controlling the release of nicotine in the pouches.

Pouch 135 (soluble matrix) surprisingly shows a fast release pattern comparable to pouch 130 where a significant amount of cellulose (insoluble matrix) is added. I.e. the cellulose does not seem to be release controlling which was contrary to the expectations. The release for pouch 135 is slightly slower than Zyn™ at 8, 16, and 30 minutes, but comparable after 60 and 120 minutes.

The marketed product Zyn™ show similar dissolution results for both 3 mg and 6 mg.

The invention claimed is:

1. A pouch designed for administration of an active ingredient in the oral cavity, the pouch containing a matrix composition comprising a water-insoluble composition, and granules consisting of a combination of nicotine and a water-soluble composition, wherein the water-soluble composition comprises sugar alcohol as a water-soluble carrier for the nicotine, and wherein the water-insoluble composition comprises microcrystalline cellulose.

2. The pouch according to claim 1, wherein said nicotine is provided as a complex between nicotine and an ion exchange resin.

3. The pouch according to claim 2, wherein said complex between nicotine and the ion exchange resin is nicotine polacrilex resin (NPR).

4. The pouch according to claim 1, wherein the nicotine is provided as a salt.

5. The pouch according to claim 1, wherein the nicotine is provided as its base form.

6. The pouch according to claim 1, wherein the water-soluble composition is a powder composition.

7. The pouch according to claim 1, wherein the matrix composition comprises a pH controlling agent.

8. The pouch according to claim 7, wherein the pH controlling agent is a buffering agent.

9. The pouch according to claim 7, wherein the pH controlling agent is a basic pH controlling agent.

10. The pouch according to claim 1, wherein the matrix composition comprises a release controlling composition.

11. The pouch according to claim 10, wherein the release controlling composition is hydrophobic.

12. The pouch according to claim 10, wherein said release controlling composition comprises one or more metallic stearates.

13. The pouch according to claim 10, wherein the matrix composition comprises said release controlling composition in an amount of between 1 and 20 percent by weight of said matrix composition.

14. The pouch according to claim 10, wherein said matrix composition comprises a first portion and a second portion, wherein said first and second portions have different contents of said release controlling composition.

15. The pouch according to claim 14, wherein both of said first and second portions comprises nicotine.

16. The pouch according to claim 15, wherein the pouch comprises a water-permeable membrane.

17. The pouch according to claim 15, wherein said matrix composition comprises nicotine in an amount of 0.1 to 30 percent by weight of said matrix composition.

18. The pouch according to claim 15, wherein the pouch comprises a humectant.

19. The pouch according to claim 15, wherein the pouch is free of tobacco.

20. A pouch designed for administration of an active ingredient in the oral cavity, the pouch containing a matrix composition comprising a water-insoluble composition, and granules consisting of a combination of nicotine and a water-soluble composition, wherein the water-soluble composition comprises sugar alcohol as a water-soluble carrier for the nicotine, wherein the nicotine is not provided as a nicotine salt, and wherein the water-insoluble composition comprises microcrystalline cellulose.

21. The pouch according to claim 18, wherein the humectant is selected from the group consisting of sugar alcohols, alginate, cellulose, microcrystalline cellulose, pectin, xanthan gum, and combinations thereof.

* * * * *